United States Patent [19]

Darby

[11] Patent Number: 5,683,373
[45] Date of Patent: Nov. 4, 1997

[54] SANITARY NAPKIN SHAPED FOR USE WITH A THONG GARMENT

[76] Inventor: Kamela J. Darby, 701 South Seas Dr. #505, Jupiter, Fla. 33477

[21] Appl. No.: 636,001

[22] Filed: Apr. 22, 1996

[51] Int. Cl.$^6$ .............................. A61F 13/15; A61F 13/20
[52] U.S. Cl. ........................................ 604/385.1; 604/387
[58] Field of Search .................................. 604/385.1, 386, 604/387, 392, 393, 395, 396, 398

[56] References Cited

U.S. PATENT DOCUMENTS

| | | |
|---|---|---|
| D. 178,455 | 8/1956 | Klein . |
| D. 191,649 | 10/1961 | Dudley . |
| D. 215,386 | 9/1969 | Glassman . |
| D. 234,162 | 1/1975 | Anderson . |
| D. 236,385 | 8/1975 | Celander et al. . |
| D. 240,562 | 7/1976 | Whitehead et al. . |
| D. 240,563 | 7/1976 | Whitehead et al. . |
| D. 240,564 | 7/1976 | Whitehead et al. . |
| D. 247,368 | 2/1978 | Whitehead . |
| 4,184,498 | 1/1980 | Franco . |
| 4,191,609 | 3/1980 | Trokhan . |
| 4,324,246 | 4/1982 | Mullane . |
| 4,342,314 | 8/1982 | Radel et al. . |
| 4,505,707 | 3/1985 | Feeney .................. 604/389 |
| 4,556,146 | 12/1985 | Swanson et al. . |
| 4,681,577 | 7/1987 | Stern et al. ............ 6604/389 |
| 4,687,478 | 8/1987 | Van Tilburg . |
| 4,804,380 | 2/1989 | Lassen et al. ........... 604/393 |
| 4,806,411 | 2/1989 | Mattingly, III et al. . |
| 4,940,463 | 7/1990 | Leathers et al. . |
| 4,950,264 | 8/1990 | Osborn, III . |
| 5,009,653 | 4/1991 | Osborn III . |
| 5,037,417 | 8/1991 | Ternstrom et al. . |
| 5,212,839 | 5/1993 | Sliman et al. ........... 604/395 |
| 5,241,710 | 9/1993 | Lockhart ................. 604/395 |
| 5,267,992 | 12/1993 | Van Tilburg . |
| 5,358,500 | 10/1994 | Lavon et al. ............ 604/391 |
| 5,383,868 | 1/1995 | Hyun . |
| 5,388,275 | 2/1995 | Oram ...................... 604/391 |
| 5,441,493 | 8/1995 | Gonzalez-Anguiano Marsel et al. . |

FOREIGN PATENT DOCUMENTS

| | | |
|---|---|---|
| 862026 | 2/1941 | France . |
| 3257949 | 4/1993 | Japan . |

*Primary Examiner*—David H. Willse
*Assistant Examiner*—Ki Yong O
*Attorney, Agent, or Firm*—Frank J. Benasutti

[57] ABSTRACT

A sanitary napkin shaped to fit the contours of a thong garment from the front of the wearer to the crotch of the wearer. The napkin is generally "V" shaped, so that the vertex of the "V" can be positioned below the vagina of the wearer. The napkin is generally V-shaped with a bulb-shaped top end and an elongated lower portion, so that the vertex of the "v" can be positioned below the vagina of the wearer.

4 Claims, 7 Drawing Sheets

SANITARY NAPKIN SHAPED FOR USE WITH A THONG GARMENT

BACKGROUND OF THE INVENTION

1. Technical Field

This invention relates to sanitary napkins designed to receive and contain vaginal discharges such as menses and more particularly to such napkins shaped to accommodate fashionable designs of clothing.

2. Background Art

There is a plethora of sanitary napkin designs to solve a wide variety of problems related to the reception, containment and disposal of the menstrual fluid issuing from a woman at the days of her menstrual period. For example, in the prior art expounded upon in U.S. Pat. No. 4,687,478 issued Aug. 18, 1987 to Kees J. Van Tillburg, et al. and assigned to The Procter & Gamble Company and his later patent based on the same application, U.S. Pat. No. 5,267,992, issued Dec. 7, 1993, there is disclosed a sanitary napkin of a particular shape with two side flaps extending outwardly from the absorbent means, each flap being associated with said absorbent means along non-linear lines of juncture. The patent is of interest for its exposition of the prior art and the problems contained therein. Those problems include reception of the fluid and containment of the fluid; comfort of the wearer; problems regarding disposal of the napkin; and retention of the napkin within the garments of the wearer as well as protection of those garments from staining. The problems also include deformation of the napkin due to conformance of the napkin with the body of the wearer. Those patents disclose, among other things, a shape of the absorbent means in which the width at its center is less than the width of its ends. The attempt is to contour this shape so it is closely attuned to the anatomical dimensions of the crotch region of the user. This ostensibly makes the sanitary napkin more comfortable to wear while, at the same time, making it more effective by rendering it less subject to compression by the legs of the user. For example, in U.S. Pat. No. 4,687,478, it is stated in column 5, lines 63 et seq., "It is preferred that the width of the central absorbent pad 212 between lines of juncture 226 and 226'at their nearest approach be from 1 to about 8 centimeters. The width of the central absorbent pad 212 at its ends should be from about 2 to 9 centimeters. Central absorbent pad 212 should be from about 7.6 to about 38 centimeters long."

Not only is it difficult to describe in such dimensional terms a device which is worn by all manner of humans in terms of their dimensions, but also, the description of this device in connection with the clothing which is to be worn by these people at the time they are wearing the device, is even more complicated. For example, at column 7 of the '478 patent beginning at line 67, it is stated:

"Total flexibility of flap 224 permits flap 224 to be positioned around the edge of the crotch portion of a panty without having to alter the natural path of the edge of the crotch portion of the panty. Thus, the edge of the crotch portion of a panty need not be stretched to fit to the second flexible axis of the flap."

The patentee goes on to describe the undergarment of the type commonly worn by many women and well known as a panty. It comprises a front section, a back section, a crotch portion which joins the front and back sections; said crotch portion comprising two side edges and a center crotch portion. Column 9, lines 40 to 45.

The patentee then goes on to define the interaction of the garment with the napkin, stating in column 10 beginning at line 11, "the edge of the crotch portion of the panty generally contains an elastic material. When a panty is worn, the elastic of the edge of the crotch portion generates an upward force, i.e., against the body due to the energy in the elastic and the fit of the panty. In accordance with this invention, the placement of a folded up wing portion on each side of the napkin between the body and the edges of the crotch portion of the panty results in an upward force generated by the edge of the crotch portion of the panty, pushing a portion of the flaps containing the second axis of flexibility snugly against the body. This results in a gasket-like seal being formed along the axis of flexibility between the flaps and the bottom. This is illustrated in FIG. 7 of the patent.

The above description is provided to show that the prior art is highly developed in its knowledge and understanding of this device and its interaction with the persons who are using this device for its intended purpose and their garments.

Sanitary napkins come in a wide variety of shapes from oblong, as shown in U.S. Pat. No. 4,556,146 issued Dec. 3, 1985 to James L. Swanson; the double-flared shape shown in the patents just mentioned and U.S. Pat. No. 4,950,264 issued Aug. 21, 1990 to Thomas W. Osborne, III and his U.S. Pat. No. 5,009,653 issued Apr. 23, 1991, as well as Design Pat. No. 215,386 issued Sep. 23, 1969 to Jacob A. Glassman. Oval shapes are also known such as that shown in Design Pat. No. 240,562 issued Jul. 13, 1976 to Howard A. Whitehead, et al., as well as their Design Pat. No. 240,563 issued Jul. 13, 1976, and Howard A. Whitehead's Pat. No. D247368 issued Feb. 28, 1978.

Other shapes include the trapezoidal shape shown in U.S. Design Pat. No. D236385 issued Aug. 19, 1975 to Robert Celander, et al., and U.S. Pat. No. D240564 issued Jul. 13, 1976 to Howard A. Whitehead, et al. and the modification of the trapezoid shown in U.S. Pat. No. D191649, dated Oct. 24, 1961, which shows the trapezoid with extensions of the type which would extend up the abdomen in the front and to the area between the buttocks in the rear; and the irregular shape of a napkin shown in U.S. Design Pat. No. D234162 patented Jan. 21, 1975 by Find Andersen.

Other attempts to contain the fluid combine the sanitary napkin with a tampon as, for example, is shown in U.S. Pat. No. 5,383,868 issued Jan. 24, 1995 to Kwang H. Hyun.

Many of these napkin designs include adhesive means to attach portions of the napkin to the clothing so that the napkin is not dislodged during use.

SUMMARY OF INVENTION

Heretofore panty shields available on the market were designed to fit a traditional full-sized woman's underwear panty. I have noted that the design is extremely uncomfortable for the growing population of women who wear thong panties and bathing suits. The back portions of the available panty shields is too large to fit in a thong fashion garment, consequently, lumping, folding and sticking outside of the garment.

To define a thong fashion from the rear is a relative task; although well known to the eye of the beholder. In general, a regular panty will embrace along its edges a portion of the thighs of the wearer. A more modified cut is known as the Rio cut in which the edges of the panty from the rear do not embrace the thighs, but rather bisect a portion of the buttocks. The thong, however, minimalizes the material between the crotch and the upper portion of the buttocks and does not flare out over any portion of the buttocks until it appears from therebetween prior to its attachment to the waistband used.

Hence, I have noted that shields would have to be custom cut in order to fit comfortably in a thong garment.

Accordingly, there are several objects and advantages of my design of an invention to fit within a thong garment. It is one object of the thong shield that it be much more convenient. The design shape will not be required to be individualized or custom-cut from a prior art napkin. Panty shields that a woman may carry in her purse to have on hand would not require precutting to fit comfortably when used because the thong garment shield would already be cut to size for such a garment. This will eliminate the waste of time in the cutting procedure and the wondering if a "guess" fit will be accurate. Further, such custom cutting normally destroys the efficacy of the devices which have been designed for particular purposes and not for the particular purpose of fitting into a thong garment.

Secondly, the thong garment shield is design to eliminate the lumping, folding, and random sticking out of the current form of panty shield worn along with the thong garment; thus considerably improving the ease of applying the shield to the thong garment in an especially comfortable manner.

The principal advantage, of course, is in the use of this device to allow the modern woman to expand the styles of underwear and other garments she wishes to use at the time of the month when she needs a sanitary napkin. This is dramatically opposed to the prior art which was obviously designed only to be useful in traditional underwear shapes.

Accordingly, it is an object of this invention to provide a sanitary napkin for use with a thong-shaped garment which provides the same degree of confidence in the actual protection being provided as in other panty shields or sanitary napkins, without jeopardizing fashion and style or risking the health of the user (as in the case of the tampon) and which ultimately eliminates all the following scenarios:

Many women during certain times of the month will change their normal fashion because there is no product available on the market to comfortably fit in the thong and french-cut styles that will provide exterior protection;

Many women will decide not to change their fashion, thus only having the option of insertable protection such as tampons with their attendant proven health risk and discomfort; and Many women will take the time and effort involved to customize their available exterior protection products to fit their underwear comfortably, but may in the process destroy the utilitarian value of such protects.

SUMMARY OF THE INVENTION

In accordance with my invention, the thong napkin provides a narrowing, tapering, anterior shape to exterior feminine protection not found in the prior art.

My invention comprises a sanitary napkin having a contour defining a first end; a second end longitudinally remote from said first end and narrower than said first end; said contour being generally V-shaped such that said second end is at the vertex of said V-shape. Most preferably, the napkin contour is further defined along longitudinally extending peripheral curvilinear edges concave from the first end to the second end and terminates in a rounded vertex. I also contemplate that the profile of said napkin taken in a plane parallel to the longitudinal side of said napkin is defined by variations in thickness from one longitudinal end to the other to provide variation in protection.

In summary, the tapering anterior design offers a slender cut to comfortably and precisely fit in thong garments. Also included are the savings in time and effort as well as the fact that women can comfortably continue to wear all fashions during their menstruation period.

From what will be described, it will be apparent that this product will also work perfectly well in all conventional and foreign fashions and provide the protection and confidence afforded by the prior art, and therefore can basically take the place of many prior art devices in many cases.

DISCLOSURE OF THE INVENTION

DESCRIPTION OF THE PREFERRED EMBODIMENT

Figure 1:
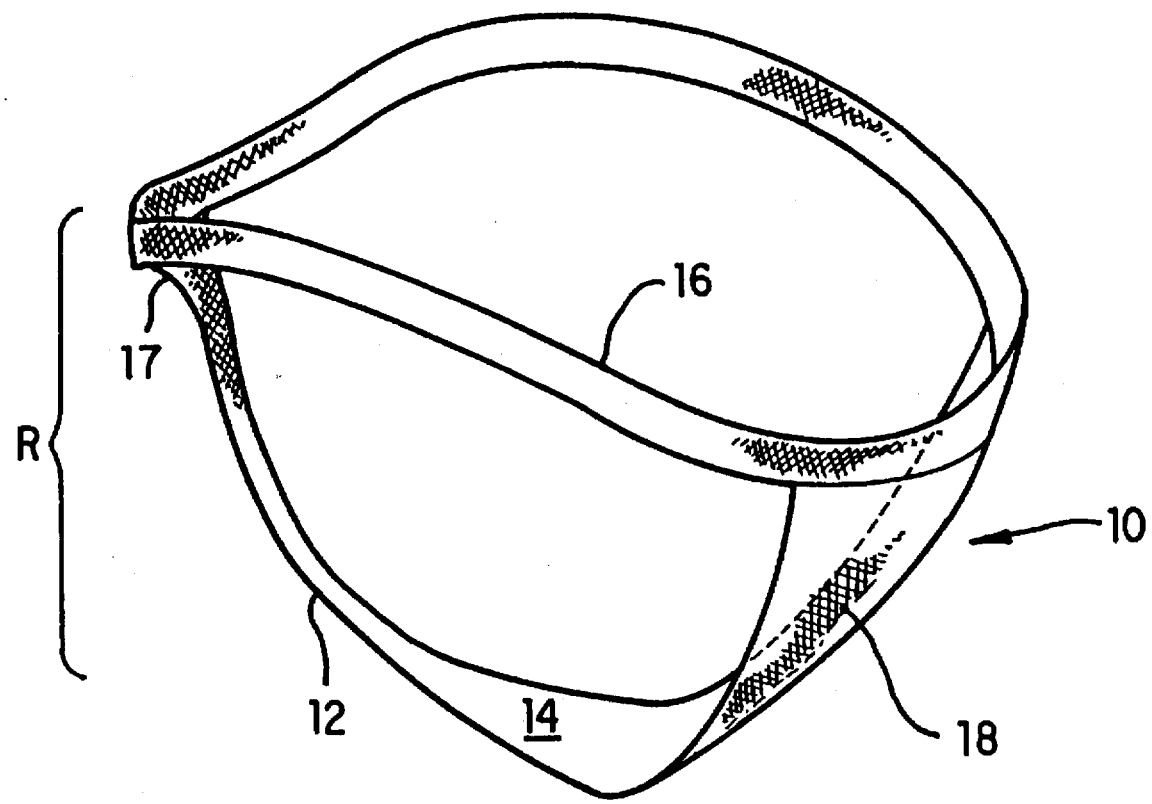
FIG. 1 is a perspective view of a typical prior art thong garment.

FIG. 1 shows a perspective view of the basic thong garment designated generally 10. This garment normally has minimal material forming the strap 12 between the crotch 14 and waistband 16 in what is the rear R of the garment. The front 18 of the garment is normally tapered and of such a width that it will only cover a portion of the abdomen of the wearer. Normally, the edges do not extend completely across the abdomen to the line of intersection between the thighs and the abdomen of the person. Any type of waistband and connection between the front and back may be used in such a thong garment. The G-string 16 is shown merely for purposes of illustration. It will also be known in the prior art to expand the amount of material at the top 17 of the strap 12 where it joins the G-string 16 in the rear, while still maintaining the narrow band up to that point; the purpose being to expose as much of the buttocks as possible. It will be appreciated by those in the fashion industry, if not those who buy such garments, that the normal panty comes with material extending down to the thigh on either side of the buttocks and that the so-called Brazilian or Rio cut has material which extends only across a portion of the buttocks up to the waistband.

Figure 2:
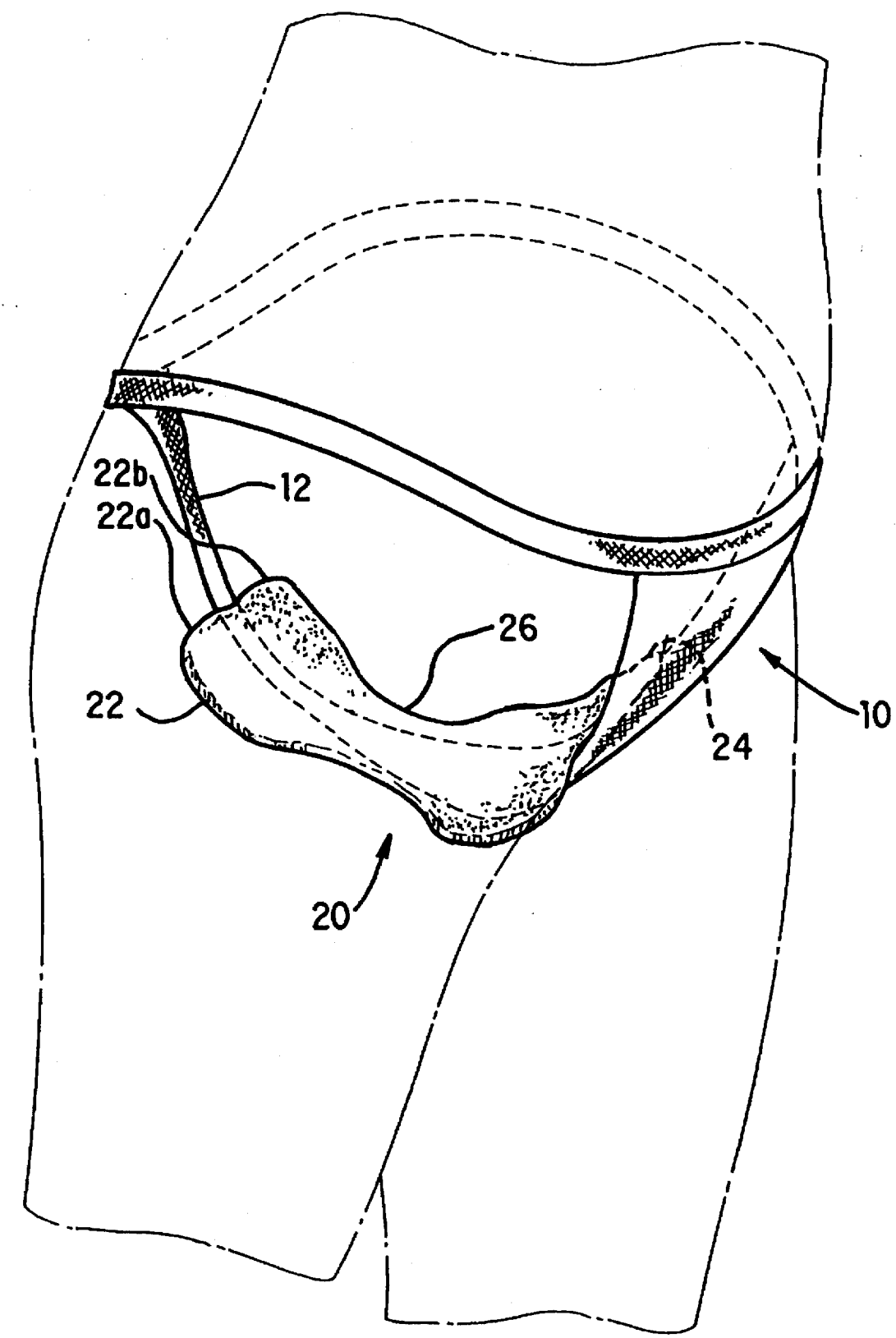
FIG. 2 is a perspective view of a typical prior art thong garment with a prior art device applied to it showing the potential wearer in phantom lines, to show positioning of the garment.
Figure 3:
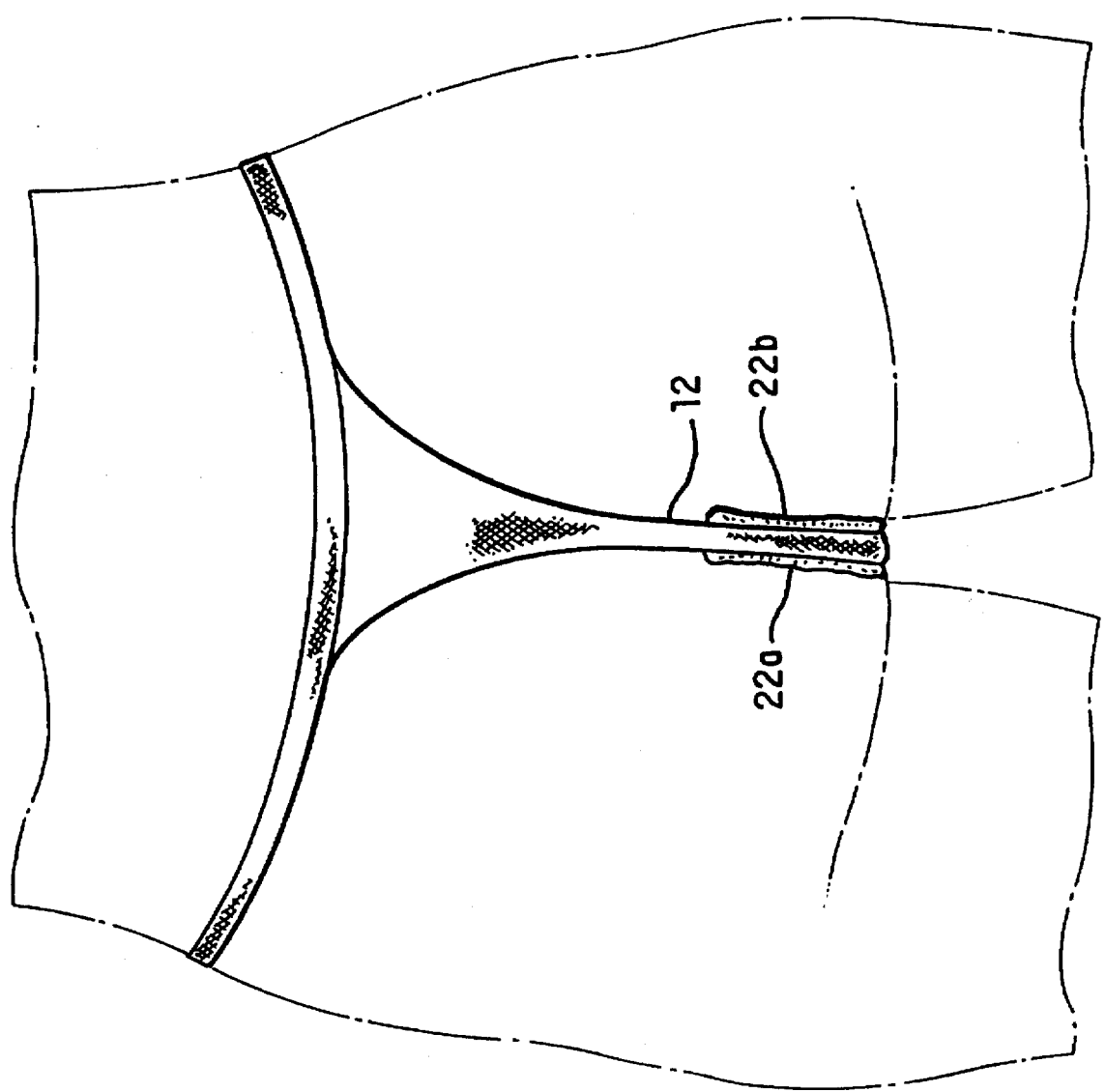
FIG. 3 is an elevation of the rear view of the prior art device shown in FIG. 2 applied to a thong garment with the resulting effects shown when the thong is worn by a person as shown in dotted lines.
Figure 3A:
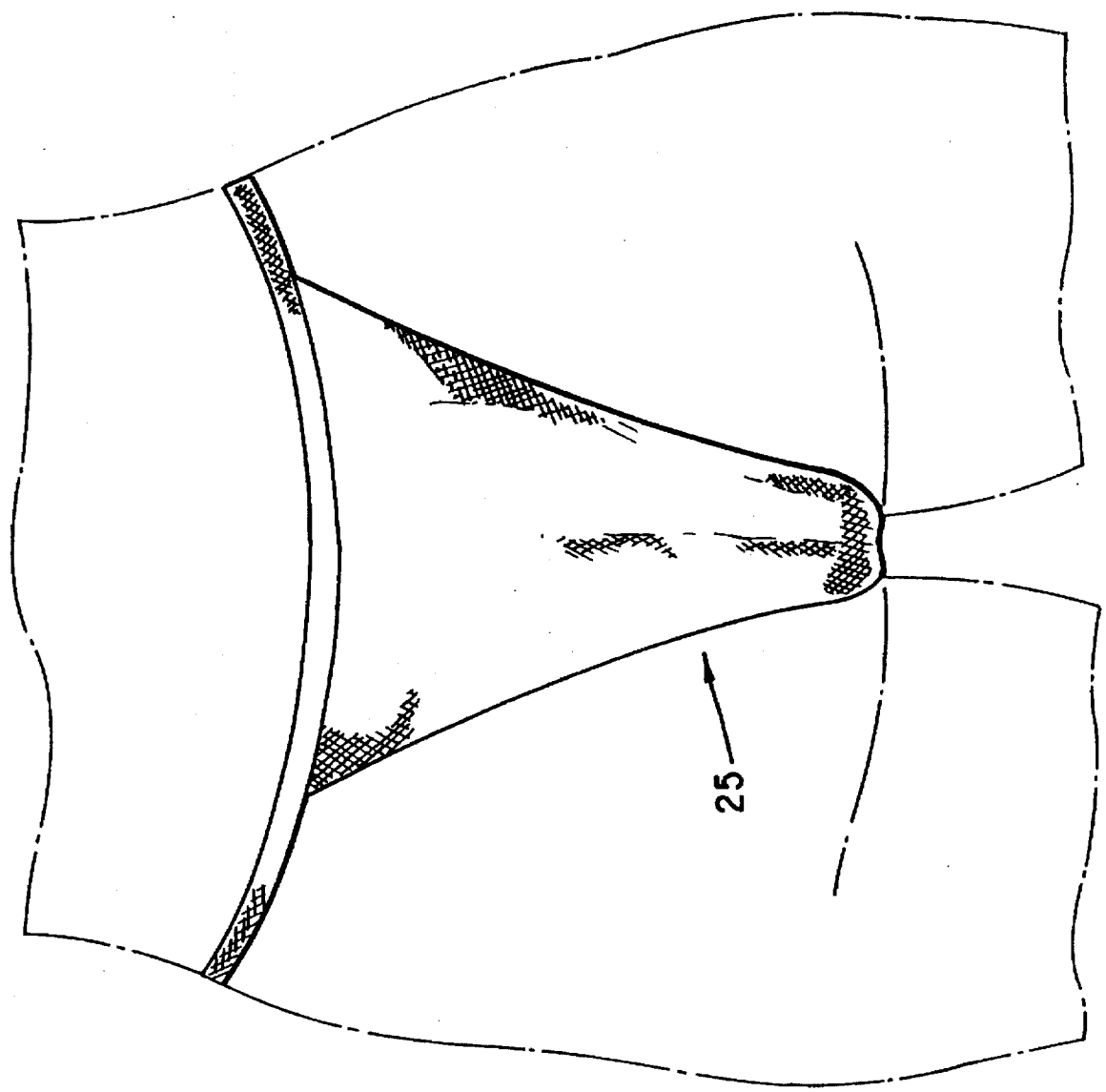
FIG. 3A is a view similar to FIG. 3, but with another prior art panty garment shown in full view.

In FIG. 2, there is illustrated the situation in which a thong garment has applied to it the usual type of panty shield as, for example, that disclosed in any number of the prior art patents described hereinabove having an elongated napkin designated generally 20 absorbent portion with wider ends 22, 24 and a narrower center 26. As will be apparent, the wider ends 22a14 22b in the buttocks portion considerably overlap the vertical strap 12 of the thong garment 10. This results in the situation shown in FIG. 3 wherein once the garment 10 is put on with the napkin 20 in place, there is a large overhang 22a and 22b on either side of the strap 12 of the garment. Indeed, many prior art devices are designed to wrap around the crotch portion of the garment, but the upper portions of the rear extension of those sanitary napkins would bunch up if they were forced between the buttocks. Indeed, thong garments are made such that the strap fits closely against the body of the user from the crotch up to the waistband. This is contrasted with prior art panties which have material from the waistband down to the thighs or even the Brazilian or Rio cut designated generally 25 in which the material extends from the waistband across a portion of the buttocks as shown in FIG. 3a.

Figure 4A:
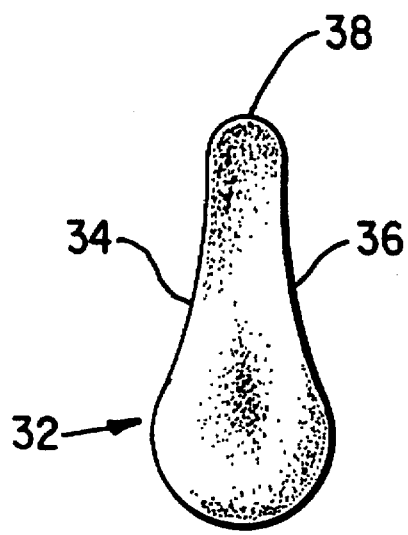
FIGS. 4 A, B and C show three plan views of the devices in accordance with my invention of different sizes.
Figure 4B:
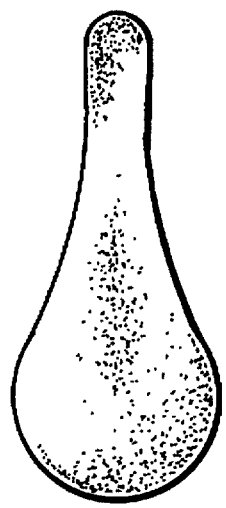
Figure 4C:
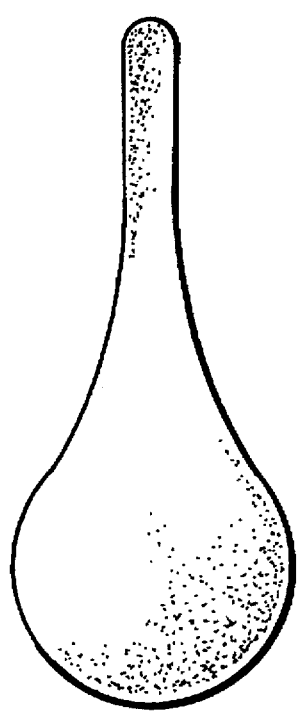
Figure 6:
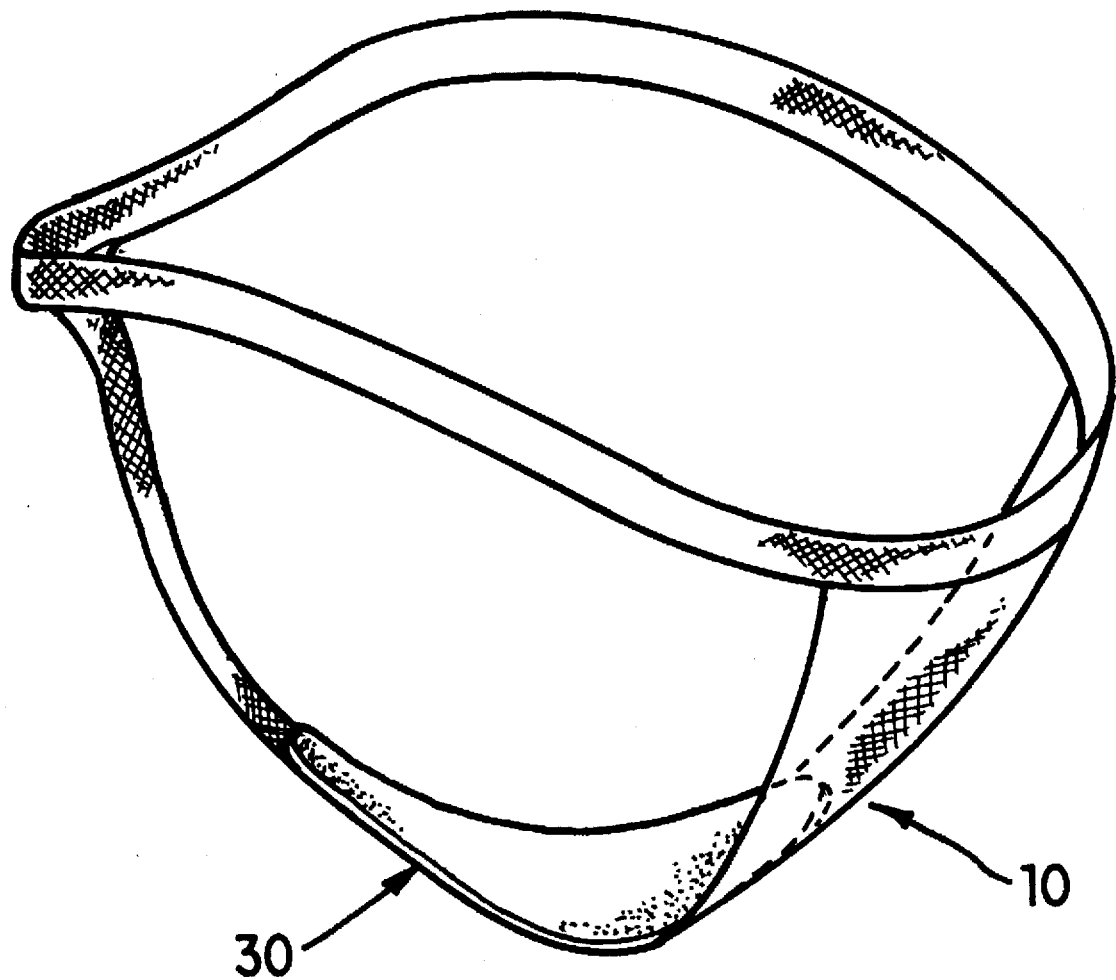
FIG. 6 is a perspective view of a thong panty shield in accordance with a preferred embodiment of my invention shown disposed in place as it would be used by a wearer of a thong (also shown)

FIG. 6 shows a perspective view of a device designated generally 30 in accordance in the preferred embodiment of this invention, in place within a thong garment 10. FIG. 4 A, B and C shows three variations of that napkin varying in accordance with size, but not necessarily in accordance with the overall shape. From those figures, it will be apparent that the portion of the sanitary napkin which would normally cover the vaginal area is wide enough and expanded long enough to cover that area comfortably while being narrow enough at one end so as not exceed the physical restraints of the size of the garment. Thus, from the widest portion designated generally 32, the napkin periphery proceeds to be concave inwardly along both edges, as at 34, 36, toward one another as it proceeds toward the opposite longitudinal end 38 of the device. That opposite longitudinal end is preferably rounded as shown and is designed to terminate just at the apex of the crotch of the user. That is to say, it is designed to terminate just beyond the lower most portion of the vagina.

The design of the front section of the panty shield remains very much the same as with other panty shields already available in the market and may vary in its contour. Thus, for example, it could have straight sides or be narrower.

The design of the end portion 38, however, is considerably different. First, it tapers much more quicker and more narrowly to a termination point than prior art devices. Secondly, it terminates far shorter than the usual designs. Finally, there is no back portion as there is in the normal design of a sanitary napkin. In sum, this design is configured to fit precisely within thong garments, such as thong panties or bathing suits.

Figure 5A:
FIGS. 5 A, B and C show left side views of the devices shown in FIGS. 4 A, B and C, respectively.
Figure 5B:
Figure 5C:
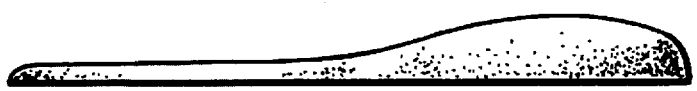

In accordance with my invention, it is desired to provide such a device in various sizes, such as small, medium and large as illustrated in FIG. 5 A, B and C.

By the same token, within each size, it would be possible within the scope of my invention to provide different thicknesses for, such as mini, regular and maxi pad protection. Further, those thicknesses could vary along the length of the device as also shown in FIG. 5 A, B and C.

It is further possible with this invention to have it retained within the confines of the garment in the usual fashion by applying adhesive means, not shown, but known per se.

METHOD OF OPERATION

Figure 7:
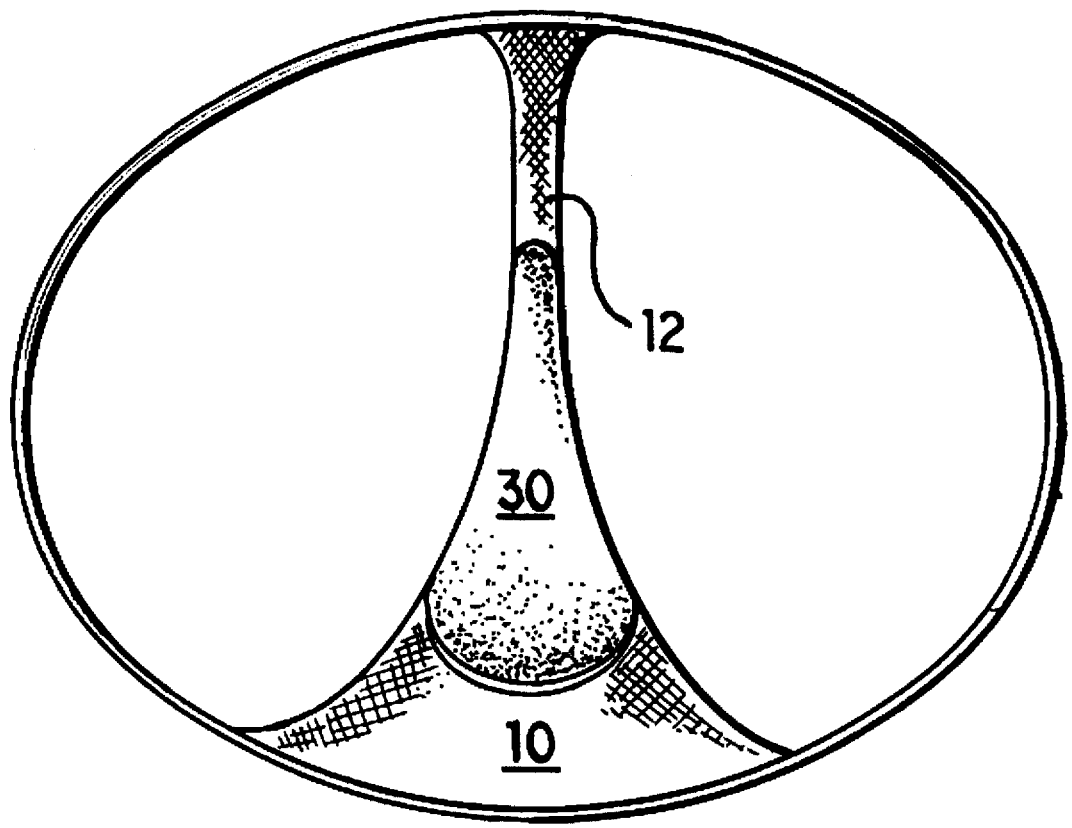
FIG. 7 is a top view of the device and garment shown in FIG. 6.

In operation, the sanitary napkin in accordance with this invention is placed in the thong garment in such a position as to fit comfortably across the lower abdomen of the person wearing the thong with the narrowest tip portion located proximate to and just beyond the lowest portion of the vagina of the wearer, as shown in top view FIG. 7. The device will stay in place by having adhesive means attaching it to the inner fabric of the thong garment. Further, it is noted that because there are no extended transverse or lateral panels on this device, it will be less likely to move from the position in which it is inserted; nor will there be any bunching up or overhang beyond the garment itself.

Thus, the invention provides comfort and ease of use, and, at times, extends to many women who would not otherwise use thong garments during the time of their period, the option of having such garments available to them.

I claim:

1. A feminine sanitary pad having one or more absorbent layers for use in absorbing menstrual fluids of a female wearer of the pad, said pad specifically adapted and configured to fit externally of the vaginal opening of said female wearer and completely within the confines of a thong-shaped garment being worn by said female, said garment having a narrow elongated crotch portion of material which extends in substantially uniform width from the crotch up the back of the garment, said pad to be positioned within said garment to extend upwardly along the inside/front of said thong garment, from a lowermost position starting just rearwardly beyond the lowermost portion of the vagina of said female, the configuration of said pad being an overall v-shaped in plan view, and bulbed at a first top end having a predetermined width, and tapering therefrom longitudinally to a midportion, and from there longitudinally narrowing in an elongated lower end portion terminating in a second end, remote from said first end, said lower end portion having a substantially uniform width, being less than twenty-five per cent of the width of said bulbed first end portion and being less than the width of the narrow elongated crotch portion of the thong garment, and a length greater than one third, but less than one half the total length of the pad from longitudinal end to end.

2. The pad of claim 1 wherein the pad has a contour which is defined along longitudinally extending peripheral curvilinear edges concave from the first end to the second end.

3. The sanitary napkin according to claim 1 wherein said second end terminates in a rounded vertex.

4. The sanitary napkin according to claim 1 wherein the side view profile of said napkin taken in a plane parallel to the longitudinal side between said two ends of said napkin is defined by variations in thickness from one end to the other.

* * * * *